US00PP12440P2

(12) United States Plant Patent
Crandall

(10) Patent No.: US PP12,440 P2
(45) Date of Patent: Mar. 5, 2002

(54) STRAWBERRY PLANT 'WHITNEY'

(75) Inventor: Beth Crandall, Watsonville, CA (US)

(73) Assignee: VPP Corporation, Oakland, CA (US)

( * ) Notice: Subject to any disclaimer, the term of this patent is extended or adjusted under 35 U.S.C. 154(b) by 0 days.

(21) Appl. No.: 09/377,341

(22) Filed: Aug. 18, 1999

(51) Int. Cl.[7] ..... A01H 5/00
(52) U.S. Cl. ..... Plt./209
(58) Field of Search ..... Plt./208, 209

(56) References Cited

PUBLICATIONS

Contract Grower 1.
Contract Grower 2.
Nursery Contract 1.
Nursery Contract 2.
Nursery Contract 3.
Nursery Contract 4.
Field Agreement 1.
Field Agreement 2.
Field Agreement 3.
Field Agreement 4.
Field Agreement 5.
Field Agreement 6.
License Agreement.
Greenhouse Agreement.

*Primary Examiner*—Bruce R. Campell
*Assistant Examiner*—June Hwu
(74) *Attorney, Agent, or Firm*—Townsend & Townsend & Crew LLP

(57) ABSTRACT

The present invention provides a new and distinct strawberry variety designated as 'Whitney.' Among the characteristics that distinguish the new variety from other closely related varieties are the timing of fruiting, plant vigor, position of the inflorescences, leaf morphology, leaf size, leaf color, and disease and pest resistance.

2 Drawing Sheets

CROSS REFERENCE TO RELATED APPLICATIONS

There are no related applications.

BACKGROUND OF THE INVENTION

The new strawberry variety claimed herein was first fruited in 1993 in a seedling field in Watsonville, Calif., east of Highway 1 and south of the Pajaro River, where it was selected, designated 92664-501, and propagated asexually by runners. The new variety resulted from a cross performed between 89530-506 and 89542-504. Asexual propagules from this original source have been tested at coastal and inland locations in Watsonville, Calif., one location in Oxnard, Calif., and one location in Plant City, Fla. With the decision that this plant was to be released, it was given the variety name 'Whitney' for the purposes of introduction into commerce and for international registration and recognition.

BRIEF SUMMARY OF THE INVENTION

The present invention relates to a new and distinct strawberry variety designated as 'Whitney.' The cultivar is botanically identified as *Fragaria.×ananassa* Duch. Among the characteristics that distinguish the new variety from other closely related varieties are the timing of fruiting, plant vigor, position of the inflorescences, leaf morphology, leaf size, leaf color, and disease and pest resistance.

DETAILED BOTANICAL DESCRIPTION

Figure 1:
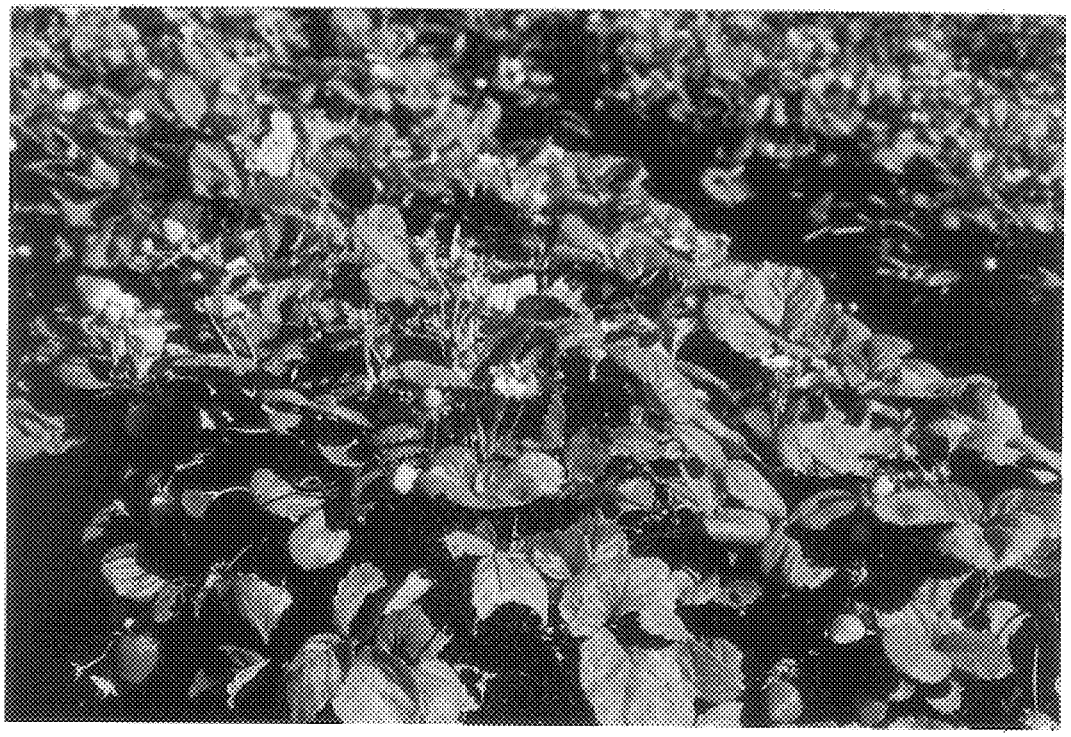
FIG. 1 depicts the general flowering and fruiting characteristics of the plant.
Figure 2:
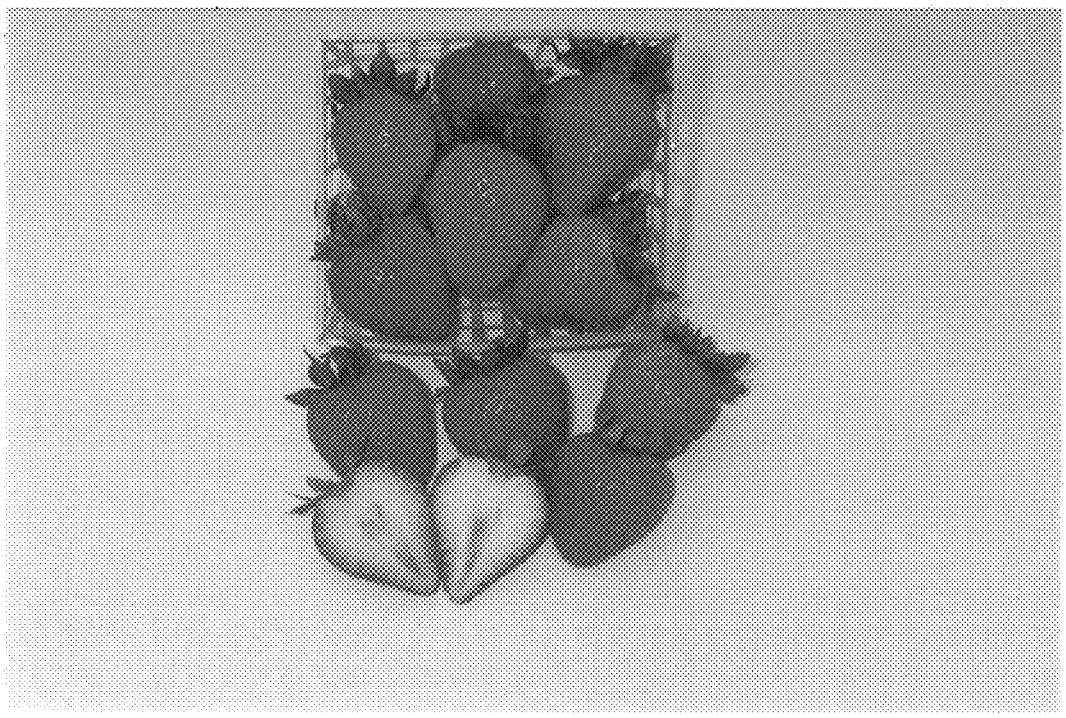
FIG. 2 depicts representative mid-season fruit.
Figure 3:
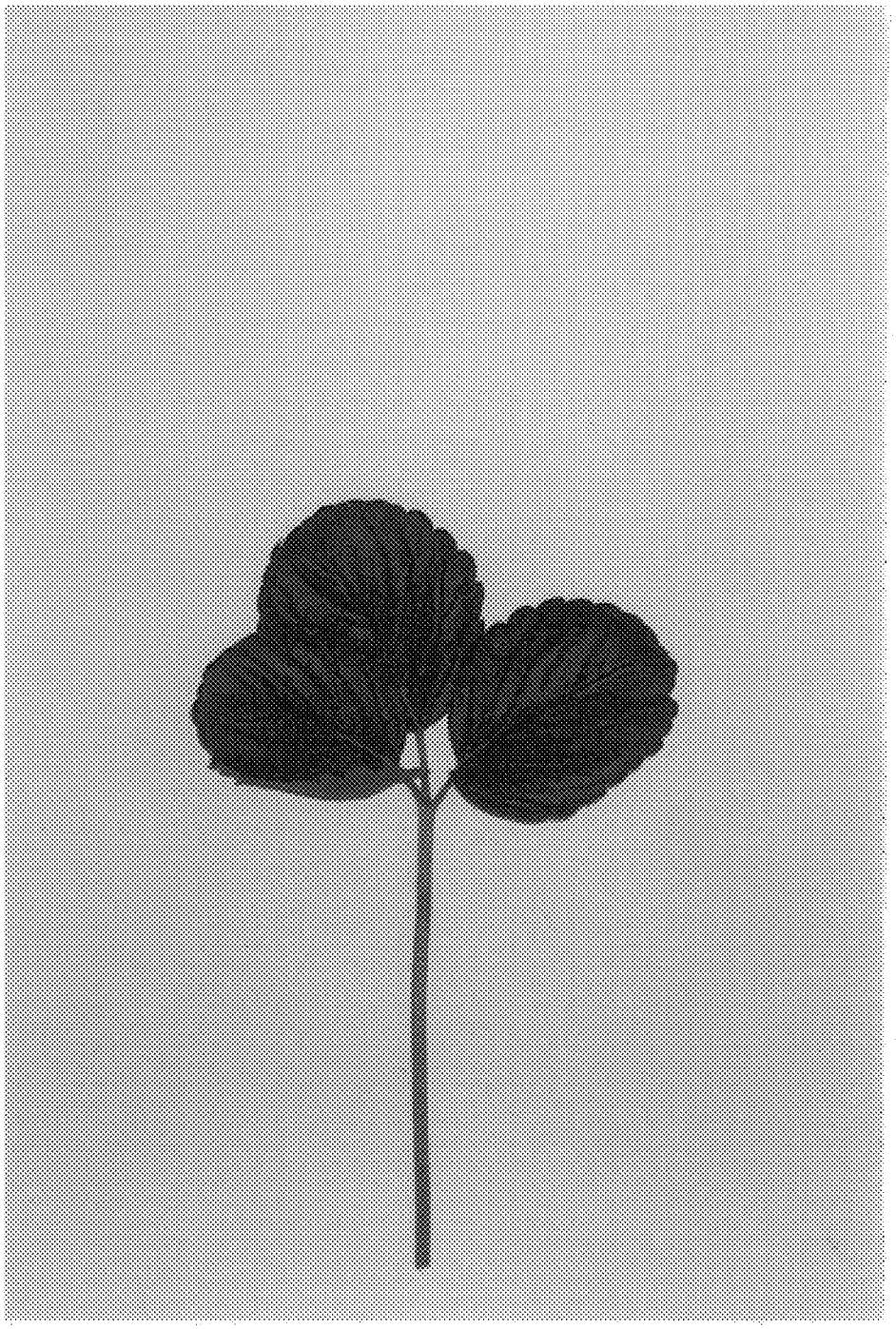
FIG. 3 depicts a typical mature leaf during late spring.

'Whitney' is a late-fruiting, everbearing light-colored, day-neutral cutlivar that has performed well in Watsonville, Calif. The plant is very vigorous and produces multiple crowns. Where it has been tested, it is competitive with the important cultivars grown in the area, although it performs better in slightly warmer areas. For example, when 'Whitney' is grown on the coast the fruit color is lighter and the yields are somewhat lower as compared to 'Whitney' grown in warmer, inland areas in the Watsonville area. 'Whitney' shows normal to good cold-hardiness. 'Whitney' fruits later than 'Selva' (U.S. Plant Pat. No. 5,266), which is a widely grown day-neutral cultivar in the Watsonville area. The following description is based on plants aged 7 to 9 months from planting.

Plants and foliage: 'Whitney' has a more vigorous plant type then 'Selva', with extremely thick crowns, petioles, and runners. The average plant height is 23 cm. The average plant spread is 38 cm. Plant vigor is moderate to good. Plant habit is semi prostrate. The plants of 'Whitney' are taller, with thicker leaves than the plants of 'Selva'. In 'Whitney', the floral structures are held more upright, on long, thick peduncles and thus the flowers are more exposed to weather but result in fruit that is highly visible and easy to pick. The leaves are palmate with 3 slightly obovate leaflets. The leaflet margins have semi-rounded serrations. Venation is 1 main vein with opposite branching. The under surface texture is moderately pubescent veins and slightly pubescent lamina. The leaves are arranged in rosettes. Leaf characteristics comparing 'Whitney' and 'Selva' are reported in Table 1. Leaflets and leaves of 'Whitney' tend to be slightly smaller than those of 'Selva', although the size is similar. Leaves of 'Whitney' tend to be slightly more convex than those of 'Selva' and have a more wrinkled surface appearance. 'Whitney' has moderate pubescence on the leaf surfaces and moderate to heavy pubescence on the petiole surface. Leaf color (using Munsell color charts) is reported in Table 2. The adaxial leaf color of 'Whitney' is very similar to that of 'Selva', although the abaxial leaf color of 'Whitney' is more yellow than that of 'Selva'. A description of petioles, stipules, stolons, peduncles, and pedicels is found in Table 3.

Isozymes in leaf extracts: 'Whitney' has been classified for three isozyme systems, using starch gel electrophoresis (Table 4). The following enzymes were analyzed: phosphoglucoisomerase (PGI), leucine aminopeptidase (LAP), and phosphoglucomutase (PGM). 'Whitney' can be distinguished from Selma by PGI phenotype. Electrophoresis was carried out according to standard techniques.

Disease and pest reaction: Disease and pest reactions of 'Whitney' and 'Selva' were observed in field situations in Watsonville. Neither cultivar was artificially inoculated. 'Whitney' shows more tolerance to two spotted spider mites (*Tetranychus urticae*) than 'Selva'. However, there are slightly higher levels of Powdery Mildew (*Sphaerotheca macularis*) in 'Whitney' than in 'Selva'.

Flowering, fruiting and production characteristics: 'Whitney' is a day-neutral cultivar. As is typical of the species, the flowers are perfect; petals are pure white and are rounded and entire; and anthers and receptacle are bright yellow. The distinguishing flower characteristics of 'Whitney' as compared to 'Selva' are shown in Table 5. The most distinctive difference between the floral characteristics of 'Whitney' and 'Selva' is the position of the flowers in 'Whitney', which are held upright and exposed. There are approximately 6 flowers per truss. The petals are rounded and are 11–14 mm in diameter. The surface texture is smooth. The stamens are 3 mm long, including the anther. Anther color is 7.5Y 7/10. Pistils are 1 mm long and color is 5Y 8/12. The adaxial surface texture of the calyx is smooth and color is 7.5GY4/4. The abaxial surface texture of the calyx is pubescent and color is 7.5GY4/4. The flowers of 'Whitney' are self-fertile and pollination is very good. Plants produced in nurseries in Northern California and planted in November in Watsonville typically begin to flower in late April and fruit begin to mature four to six weeks later. The fruit shape is conic and under adverse weather conditions some of the fruit may be misshapen. Fruit varies in size, with smaller fruit having solid centers and larger fruit having a small hollowing in the center. Although the fruit quality of 'Whitney' is very high, the fruit is lighter in color than 'Selva' with a high gloss and yellow to brown achenes. The internal color of 'Whitney' is very light with an almost white center. The fruit of 'Whitney' is slightly less firm than 'Selva'. Fruit aroma is very sweet and lacks acidity. Average fruit weight is 24 grams/fruit. Fruit length is 48.5 mm. Fruit width is 46.5 mm across the shoulders. Fruiting is continuous from May to October in Watsonville, Calif. Harvest of 'Whitney' begins later than harvest of 'Selva', but overall yields are comparable. 'Whitney' has a major peak in fruit production in July, then gaps slightly and re-fruits again for the later season market. Average fruit weight of 'Whitney' is slightly lower then 'Selva' due to slightly smaller fruit size. 'Whitney' is recommended for a fresh market cultivar and is competitive in California because of its fruit quality and fruit production patterns.

TABLE 1

Foliar Characteristics for 'Whitney' and 'Selva'

| Foliar Character | Cultivar 'Whitney' | Cultivar 'Selva' |
|---|---|---|
| Mid-tier leaflet Length (mm) | | |
| mean | 71.45 | 72.6 |
| range | 56–100 | 65–88 |
| Mid-tier leaflet Width (mm) | | |
| mean | 67.65 | 68.2 |
| range | 53–87 | 51–84 |
| Mid-tier leaflet Length (mm) | | |
| mean | 87.2 | 119.2 |
| range | 60–100 | 94–139 |
| Mid-tier leaflet Width (mm) | | |
| mean | 144.15 | 130.1 |
| range | 120–206 | 111–170 |
| # of leaflets/leaf | 3 | 3 |
| Leaf Convexity | flat to convex | mostly flat to convex |
| Leaf Serrations | | |
| number | moderate | few to moderate |
| shape | semi-round | round to semi-pointed |
| Leaf Pubescence | moderate | moderate |
| Petiole Pubescence | moderate to heavy | heavy |

TABLE 2

Leaf and fruit color characteristics for 'Whitney' 'Selva'

| Character | Cultivar 'Whitney' | Cultivar 'Selva' |
|---|---|---|
| Leaf color Adacial | 7.5GY 4/4 | 7.5GY 4/4 |
| Leaf Color Abaxial | 2.5GY ¾ | 2.5G 3/3 |
| External Fruit Color | 7.5R 4/10 | 5R 4/12 |
| Internal Fruit Color | N9.25/84% with 7.5R 4/10 at center | 5R 5/13 |

All color From the Munsell Color system

TABLE 3

Characteristics of Petioles, Stipules, Stolons, Peduncles, and Pedicels

| | Average Number | Munsell Color | Length (cm) | Width (mm) | Surface Texture |
|---|---|---|---|---|---|
| Petioles | 22.5 | 5GY 7/6 | 8–18 | 3–6 | Smooth, moderately pubescent |
| Stipules | In pairs on all nodes | 5GY 7/6 | 1–1.9 | 6 | Smooth, moderately pubescent |
| Stolons | 0–0.5/plant | 5GY 7/6 | 10–25 | 3–5 | Smooth, moderately pubescent |
| Peduncles | 8/plant | 5GY 7/6 | 5–10 | 5–9 | Smooth, moderately pubescent |
| Pedicels | 6/peduncle | 5GY 7/6 | 5–13 | 2–5 | Smooth, moderately pubescent |

TABLE 4

Isozyme phenotypes for 'Whitney' 'Selva'

| Locus | Cultivar 'Whitney' | Cultivar Selva |
|---|---|---|
| PGI | A4 | A2 |
| LAP | B3 | B3 |
| PGM | C2 | C2 |

Table 5

Flower and Fruit Characters for 'Whitney' and 'Selva'

| Character | Cultivar 'Whitney' | Cultivar Selva |
|---|---|---|
| Number of Petals | | |
| mean | 5.4 | 5.8 |
| range | 5–7 | 5–8 |
| Flower position (relative to foilage) | exposed to even | even or interior |
| Calyx Diameter (mm) | | |
| mean | 35.2 | 29 |
| range | 31–40 | 22–35 |

Table 5-continued

Flower and Fruit Characters for 'Whitney' and 'Selva'

| Character | Cultivar 'Whitney' | Cultivar Selva |
|---|---|---|
| Corolla Diameter (mm) | | |
| mean | 33.2 | 37.5 |
| range | 30–39 | 31–43 |
| Fruit shape (length to width) | | |
| ratio | 1.04 | 1.16 |
| range | 0.9–1.3 | 1.02–1.25 |
| subjective | conic | conic to flat conic |
| Calyx Position | reflexed to slightly reflexed | even with shoulder |
| Seed Position | even to slighty extruded | even to slighty extruded |

What is claimed is:

1. The new and distinct cultivar of strawberry plant substantially as herein described and illustrated.

* * * * *